(12) United States Patent
Yoshikawa et al.

(10) Patent No.: US 12,600,677 B2
(45) Date of Patent: Apr. 14, 2026

(54) CERAMIC GREEN SHEET LAMINATION AID AND CERAMIC GREEN SHEET COMPOSITION

(71) Applicant: NOF CORPORATION, Tokyo (JP)

(72) Inventors: Fumitaka Yoshikawa, Kawasaki (JP); Kenta Matsuzaki, Kawasaki (JP); Kazuki Sunada, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 1141 days.

(21) Appl. No.: 17/435,732

(22) PCT Filed: Mar. 5, 2020

(86) PCT No.: PCT/JP2020/009320
§ 371 (c)(1),
(2) Date: Sep. 2, 2021

(87) PCT Pub. No.: WO2020/179856
PCT Pub. Date: Sep. 10, 2020

(65) Prior Publication Data
US 2022/0135488 A1    May 5, 2022

(30) Foreign Application Priority Data
Mar. 6, 2019    (JP) ................................. 2019-040143

(51) Int. Cl.
| | |
|---|---|
| *C04B 35/634* | (2006.01) |
| *C04B 35/10* | (2006.01) |
| *C04B 35/468* | (2006.01) |
| *C07C 43/10* | (2006.01) |
| *H01G 13/00* | (2013.01) |
| *H01G 4/30* | (2006.01) |

(52) U.S. Cl.
CPC .......... *C04B 35/6342* (2013.01); *C04B 35/10* (2013.01); *C04B 35/4682* (2013.01); *C07C 43/10* (2013.01); *C04B 2235/3217* (2013.01); *C04B 2235/3236* (2013.01); *H01G 4/30* (2013.01); *H01G 13/00* (2013.01)

(58) Field of Classification Search
None
See application file for complete search history.

(56) References Cited

U.S. PATENT DOCUMENTS

| | | | |
|---|---|---|---|
| 9,193,654 B2 | 11/2015 | Maruyama et al. | |
| 10,995,178 B2 * | 5/2021 | Hara ...................... | C08G 18/48 |
| 2020/0190260 A1 * | 6/2020 | Hara ...................... | C08G 65/08 |

FOREIGN PATENT DOCUMENTS

| | | | | | |
|---|---|---|---|---|---|
| CN | 101052371 A | | 10/2007 | | |
| JP | 61-222953 A | | 10/1986 | | |
| JP | 07-025665 A | | 1/1995 | | |
| JP | 07-033533 A | | 2/1995 | | |
| JP | H0733533 A | * | 2/1995 | ........... | C04B 35/622 |
| JP | 2001-106580 A | | 4/2001 | | |
| JP | 2007-261911 A | | 10/2007 | | |
| JP | 2010-181252 A | | 8/2010 | | |
| JP | 2011-96754 A | | 5/2012 | | |
| JP | 2013023662 A | * | 2/2013 | .......... | C10M 105/14 |
| JP | 2018-143969 A | | 9/2018 | | |
| WO | 2006/038724 A1 | | 4/2006 | | |
| WO | WO-2018030283 A1 | * | 2/2018 | ............. | C08G 65/08 |

OTHER PUBLICATIONS

Machine Translation of JP-2013023662-A (Year: 2013).*
Machine Translation of JP-H0733533-A (Year: 1995).*
Notification of Reasons for Refusal dated Dec. 12, 2022 from the Japanese Patent Office in Application No. 2021-503641.
Communication dated May 24, 2023 issued by the Japanese Patent Office in application No. 2021-503641.
International Search Report of PCT/JP2020/009320 dated May 26, 2020 [PCT/ISA/210].

* cited by examiner

*Primary Examiner* — Amber R Orlando
*Assistant Examiner* — Paul Alan Forsyth
(74) *Attorney, Agent, or Firm* — Sughrue Mion, PLLC

(57) ABSTRACT

A ceramic green sheet lamination aid including a compound represented by formula (1).

$$Z—[O-(AO)n-H]x \qquad (1)$$

wherein Z represents a residual group of a compound having a number of carbons group of 1 to 22 and having hydroxyl groups of 1 to 6 in which all of the hydroxyl groups are removed; x represents a number of 1 to 6; AO represents an oxyalkylene group having a number of carbons of 2 to 4; n represents a number of 5 to 500; x×n is in a range of 5 to 500; and a weight ratio of oxyethylene group EO contained in the oxyalkylene group AO having the number of carbons of 2 to 4 is 0 to 80 weight %.

3 Claims, No Drawings

CERAMIC GREEN SHEET LAMINATION AID AND CERAMIC GREEN SHEET COMPOSITION

CROSS REFERENCE TO RELATED APPLICATIONS

This application is a National Stage of International Application No. PCT/JP2020/009320, filed Mar. 5, 2020, claiming priority to Japanese Patent Application No. 2019-040143, filed Mar. 6, 2019.

TECHNICAL FIELD

The present invention relates to a lamination aid used in a step of laminating ceramic green sheets and a ceramic green sheet composition containing the lamination aid. More specifically, it relates to a lamination aid which can suppress peeling and lamination misalignment of the ceramic green sheets at a small addition amount and can suppress the reduction of sheet strength and increase of residue during the sintering, and a ceramic green sheet composition containing the lamination aid.

BACKGROUND ARTS

Electronic parts such as multilayer ceramic capacitors (MLCC), multilayer chip inductors or the like are mainly produced by steps of laminating green sheets each composed of a ceramic such as barium titanate or ferrite or a binder resin.

Recently, as the miniaturization and improvement of performances of electronic appliances, it has been demanded the miniaturization and increase of the capacity of the MLCC. The miniaturization and increase of capacity can be realized by thin the ceramic green sheets and conductive layers, which are constituting parts, and by producing multi-layered structure.

As the strength of the green sheet is reduced due to the thinning of the film, problems are provided such as the fracture of the green sheet upon the lamination. Thus, binders of high strengths are selected in many cases, and for example, polyvinyl butyral has been widely applied. However, as the hardness of the binder of high strength is higher than those of prior binders, the adhesiveness between the sheets tends to be lowered than that of prior articles. As the adhesiveness is lowered, the peeling of the layers may be generated during the lamination and thermal pressing steps of the green sheets, resulting in defects.

In the case that the adhesiveness of the green sheets is deteriorated, a large amount of a plasticizer can be added to the resin to obtain adhesive property. However, as the resin is softened and the strength of the resin is lowered, the resin is deformed during the thermal pressing step so that the precision of dimensions is deteriorated. It is thus necessary to obtain the adhesiveness and strength of the resin at the same time. For solving such object, it is shown the method of combining polyvinyl butyral and a specific plasticizer to suppress the peeling of the layers without lowering the strength of the resin, in patent document 1.

PRIOR TECHNICAL DOCUMENTS (Patent Document)
(Patent document 1) Japanese Patent Publication No. 2001-106580A

SUMMARY OF THE INVENTION

Object to be Solved by the Invention

However, recently, as the layers of the green sheets are made thinner and a number of the layers is increased, the green sheets are more and more susceptible to defects. Particularly, in the case that a load is applied during the lamination and thermal pressing steps, the green sheets slip to generate lamination misalignment, resulting in the instability of quality of products. For solving such problem, it is proved to be insufficient to prevent the peeling of the layers according to the prior art. It is thus demanded the method of suppressing the lamination misalignment during the lamination and thermal pressing steps.

As described above, an object of the present invention is to suppress the peeling and lamination misalignment of ceramic green sheets without deteriorating the sheet strength.

Solution for the Object

As the inventors have extensively researched for solving the object, it is found that the object described above can be solved by a polyether compound having a specific structure.

That is, the present invention provides the following (1) and (2).

(1) A ceramic green sheet lamination aid comprising a compound represented by formula (1).

$$Z—[O-(AO)n-H]x \qquad (1)$$

(In the formula (1),

Z represents a residual group of a compound having a number of carbons of 1 to 22 and 1 to 6 hydroxyl groups wherein all the hydroxyl groups are excluded, x represents a number of 1 to 6, AO represents an oxyalkylene group having a number of carbons of 2 to 4, n represents a number of 5 to 500, x×n is in a range of 5 to 500, and the weight ratio of oxyethylene group EO contained in the oxyalkylene group AO having the number of carbons of 2 to 4 is 0 to 80 weight %.)

(2) A ceramic green sheet composition comprising 0.01 to 5 mass % of a component (A) described below, 1 to 25 mass % of a component (B) described below and 70 to 98 mass % of a component (C) described below.

the component (A): the ceramic green sheet lamination aid of claim 1 the component (B): polyvinyl butyral the component (C): a ceramic powder

Effects of the Invention

According to the present invention, it is possible to suppress the peeling and lamination misalignment of the ceramic green sheets without the reduction of the sheet strength or increase of residue generated during the sintering.

EMBODIMENTS FOR CARRYING OUT THE INVENTION

It will be described below the lamination aid of the present invention and the ceramic green sheet composition containing the lamination aid.

(Lamination Aid)

The lamination aid of the present invention is a polyether compound represented by the following formula (1).

$$Z-[O-(AO)n-H]x \qquad (1)$$

Z in the formula (1) is a residual group of an alcohol compound having a number of carbons of 1 to 22 and 1 to 6 hydroxyl groups in which all the hydroxyl groups are excluded. That is, the alcohol compound is represented by (Z(OH)x), and Z is the residual group of the alcohol compound from which all the (OH) are excluded. Such alcohol compound may be methanol, ethanol, n-butanol, n-octanol, 2-ethyl hexanol, 3,5,5-trimethyl hexanol, dodecanol, octadecanol, behenyl alcohol, ethylene glycol, propylene glycol, butylene glycol, pentane diol, hexane diol, octane diol, glycerin, 1,2,3-butane triol, 1,2,4-butane triol, 1,2,5-pentane triol, 1,2,3-cyclohexane triol, 1,3,5-cyclohexane triol, 1,2,6-cyclohexane triol, 3-methyl pentane-1, 3, 5-triol, diglycerin, 1, 2, 3, 4-butane tetraol, erythritol, pentaerythritol, sorbitan, triglycerin, glucose, ribitol, xylitol, mannose, sorbitol, mannitol or the like.

The number of carbons of z may more preferably be 2 or higher, and more preferably be 10 or lower and most preferably be 5 or lower.

x in the formula (1) is a number of the AO chains connected to Z, and corresponds with the number of hydroxyl group of the alcohol (Z(OH)x). x is 1 to 6, preferably 1 to 5, more preferably 1 to 4, and most preferably 1 to 3. In the case that x exceeds 6, the viscosity of the lamination aid is high and the handleability may be deteriorated. On such viewpoint, as the alcohol, it is preferred to use methyl alcohol ethyl alcohol, butyl alcohol, 2-ethyl hexanol, 3,5,5-trimethyl hexanol, ethylene glycol, propylene glycol or glycerin, and it is more preferred to use methyl alcohol, butyl alcohol, ethylene glycol or glycerin.

AO in the formula (1) is oxyalkylene group having a number of carbons of 2 to 4, and specifically obtained by addition polymerization of ethylene oxide, propylene oxide or butylene oxide. As the alkylene oxide, it is preferred to use ethylene oxide or propylene oxide and most preferably be propylene oxide, on the viewpoint of suppressing the lamination misalignment. Further, one or two or more kinds of them may be combined. In the case that 2 or more kinds are subjected to the addition, the order is not particularly relevant and block type and random type may be selected. Random type addition is preferred on the viewpoint of suppressing the reduction of the strength of the ceramic green sheet.

n represents an average molar number added of AO and a number of 5 to 500, and in the case that two or more kinds of AO are included, n represents a total of the average molar numbers of the respective AO's.

The average molar number added (x×n) of all the AO's in the formula (1) is 5 to 500. x×n is preferably 25 to 500, more preferably 10 to 450, still more preferably 25 to 450, still more preferably 30 to 450, particularly preferably 50 to 400, and most preferably 50 to 200. In the case x×n is below 5, the peeling and lamination misalignment of the ceramic green sheets may not be sufficiently suppressed and the sheet strength may be possibly lowered. In the case that (x×n) exceeds 500, the viscosity of the lamination aid is high and the handleability is deteriorated.

Although the lamination aid of the present invention may contain oxyethylene group (EO) on the viewpoint of improving the solubility with a resin, the upper limit of the weight ratio of EO contained in AO (weight of EO/weight of AO×100) is 80 weight %. The weight ratio of EO contained in AO may preferably be 0 to 60 weight % and more preferably be 0 to 50 weight %. In the case that the weight ratio of EO contained in AO exceeds 80 weight %, although the solubility into the resin is increased, the strength may be lowered.

The molecular weight of the lamination aid of the present invention can be measured by gel permeation chromatography and may preferably be 500 to 35000, more preferably 2000 to 35000, still more preferably 2500 to 30000, particularly preferably 3000 to 25000 and most preferably 3000 to 10000. In the case that the molecular weight exceeds 35000, the viscosity of the polyether compound shown in the formula (1) becomes high, so that the handleability may be deteriorated and the solubility into a solvent tends to be deteriorated. On the other hand, in the case that molecular weight is lower than 500, the peeling and lamination misalignment of the ceramic green sheets may not possibly be sufficiently suppressed and the sheet strength may possibly be lowered.

(Ceramic Green Sheet Composition)

The ceramic green sheet composition of the present invention contains 0.01 to 5 mass % of the lamination aid (component (A)), 1 to 25 mass % of polyvinyl butyral (component (B)) and 70 to 98 mass % of a ceramic powder (component (C)).

Further, 100 mass % is assigned to a total of the amounts of the component (A), component (B) and component (C).

The content of the lamination aid of the present invention is 0.01 to 5 mass %, preferably 0.05 to 3 mass % and more preferably 0.1 to 2 mass %. In the case that the content of the lamination aid is lower than 0.01 mass %, the peeling and sliding of the green sheets cannot be sufficiently suppressed. On the other hand, in the case that the content of the lamination aid exceeds 5 mass %, the strength of the green sheet may possibly be insufficient.

Although polyvinyl butyral (component (B)) in the ceramic green sheet composition is not limited as far as it is generally used in the green sheets, as the molecular weight is higher, the adhesiveness of polyvinyl butyral tends to be insufficient. The weight average molecular weight of polyvinyl butyral may preferably be 500000 or lower, more preferably be 300000 or lower and most preferably be 200000 or lower. Further, as it is demanded the strength for responding to the thinning of the green sheet, the weight average molecular weight of polyvinyl butyral may preferably be 50000 or higher and more preferably be 100000 or higher.

The content of polyvinyl butyral is 1 to 25 mass %, preferably 1 to 15 mass % and most preferably 3 to 10 mass %.

The ceramic powder (component (C) in the ceramic green sheet composition is not limited as far as it is generally used in the green sheets. It may be powder of silicate minerals, the other silicate compounds, carbonate compounds, sulfate compounds, hydroxide compounds, oxide compounds, nitride compounds, carbide compounds, titanate compounds or the like. For example, it may be powder of each of kaolin, clay, talc, mica, bentonite, dolomite, calcium silicate, aluminum silicate, magnesium silicate, calcium carbonate, magnesium carbonate, barium carbonate, calcium sulfate, barium sulfate, aluminum sulfate, aluminum hydroxide, iron hydroxide, zirconium oxide, magnesium oxide, aluminum oxide, titanium oxide, iron oxide, zinc oxide, antimony trioxide, indium oxide, indium tin oxide, silicon carbide, tungsten carbide, aluminum nitride, silicon nitride, boron nitride, barium titanate, calcium titanate, strontium titanate, carbon black, glass fiber, carbon fiber, carbon nano fiber, carbon nano tube (single wall nano tube, double wall nano tube, multi wall nano tube) or the like.

The ceramic powder is preferably powder of each of oxide compounds such as zirconium oxide, magnesium oxide, aluminum oxide, iron oxide, zinc oxide, indium tin oxide and the like, titanate compounds such as barium titanate, calcium titanate, strontium titanate. The powder of titanate compound is more preferred and powder of barium titanate is most preferred.

Although the average grain size of the ceramic powder is not particularly limited, there is the tendency that it is used ceramic powder having a lower average grain size as the film thickness of the green sheet is made smaller. On the viewpoint, it is preferred to combine with the ceramic powder having an average grain size of 300 nm or smaller and more preferred to combine the ceramic powder having an average grain size of 50 to 200 nm. Further, the average grain size of the dispersed body can be measured by electron microscope method by means of an SEM (scanning type electron microscope) or TEM (transmission type electron microscope) or micro track method (laser diffraction•scattering method).

The content of the ceramic powder is 70 to 98 mass %, preferably 80 to 95 mass % and more preferably 85 to 95 mass %.

The ceramic green sheet composition may contain, as common components, the other ceramic additive, a plasticizer, dispersing agent, antistatic agent or the like, in addition to the blended components described above. Particularly, by combining the plasticizer and the inventive lamination aid, it is possible to effectively suppress the peeling and lamination misalignment of the layers. In this case, provided that 100 mass parts are assigned to a total amount of the components (A), (B) and (C), the content of the plasticizer may preferably be 0.01 to 20 mass parts and more preferably be 0.1 to 10 mass parts.

Further, as the dispersing agent, it may be generally used a polymer having, as a side chain, a polar group such as hydroxyl group, carboxyl group, polyether group or amino group, and the polymer having both of the polyether group and carboxyl group is preferred. The polymer may be the polymer of vinyl ether having polyoxyalkylene group and maleic anhydride. In the case that the dispersing agent is added, provided that 100 mass parts are assigned to the total amount of the components (A), (B) and (C), the content of the dispersing agent may preferably be 0.01 to 20 mass parts and more preferably be 0.1 to 10 mass parts.

A solvent may be added into the composition. Such solvent may be ketone solvents such as acetone or methyl ethyl ketone, alcohol solvents such as ethanol or isopropanol, and aromatic solvents such as toluene, xylene or the like. The solvents mat be used alone or two or more kinds of the solvents may be used in combination. It is preferred to use the alcohol and aromatic solvents. In the case that the solvent is added, provided that 100 mass parts are assigned to the total amount of the components (A), (B) and (C), the content of the solvent may preferably be 20 to 500 mass parts and more preferably be 50 to 300 mass parts.

EXAMPLES

Although the present invention will be described further in detail below, referring to the examples, the present invention is not limited to the examples in any sense.
(Lamination Aid)

As the lamination aids, the lamination aids 1 to 7 and comparative articles 1 and 2 having the compositions shown in table 1 were used. EO and PO in the lamination aids 3 and 4 in table 1 were added in random addition mode and EO and PO in the lamination aids 6 and 7 were added in block addition mode in the order of EO-PO.
(Molding 1 of Ceramic Green Sheets)

Media with a particle size of 2 mm and made of YTZ were filled in a 0.5-liter polyethylene pot in 50 vol. %, and the respective materials were charged into the pot in the respective compositions shown in tables 2, 3 and 4. After it was agitated by means of MASUDA UNIVERSAL BALL MILL MODEL UBM-2 at a rotation rate of 60 rpm for 5 hours, the media were filtered to obtain ceramic composition slurry.

The thus obtained slurry was applied on a PET film by means of a doctor blade coater at a molding speed of 1.5 m/min. At the step, the groove width of the blade was made 140 μm, and the PET film having a thickness of 32 μm was used. Further, the applied slurry was dried at 40° C., 60° C., 75° C. or 85° C. for 10 minutes, respectively, to obtain target ceramic green sheets.
(Sheet Properties and Adhesiveness)

The sheet strength, adhesive strength and coefficient of static friction were evaluated according to the following method. The results were shown in tables 2, 3 and 4.
(Method of Measuring Sheet Strength)

Test pieces each having a width of 3 cm and length of 10 cm were produced using the respective green sheets described in the tables. The tensile strengths (N/mm$^2$) of the test pieces were measured by means of MODEL 9502B supplied by AIKOH. The results were evaluated based on the following standard.

⊚: 16.0 (N/mm$^2$) or more
○: 15.0 to 16.0 (N/mm$^2$)
X: less than 15.0 (N/mm$^2$)
(Method of Measuring Adhesive Strength of the Sheets)

The respective green sheets described in the table were laminated and then pressure-pressed at 500 kg/cm$^2$ and 60° C. for 1 minute. The pressure-pressed green sheets were cut in a width of a width of 2.5 cm and length of 25 cm to produce test pieces. Referring to JIS K-6854-1 (Determination of peel strength of bonded assemblies), one surface of each of the test pieces was fixed on a table and the other surface was pulled by means of "MODEL 9502B" supplied by AIKOH at 500 mm/minute to peel the adhesive surface. The force [N] required at the time was divided by the width of the test piece to calculate the adhesive strength (N/m). The results were evaluated based on the following standard.

⊚: 15.0 [N/m] or larger
○: 10.0 to 15.0 [N/m]
X: smaller than 10.0 [N/m]
(Method of Measuring Friction Coefficient Between the Sheets)

The coefficients of static friction and dynamic friction between the sheets of the respective green sheets described in the tables were measured. The coefficients were measured by means of a friction tester (Model: TL201Tt, supplied by Trinity Labo corporation) and the green sheets were adhered at a region (a square of 1 cm×1 cm) where a contact pad contacts the sample, so that the friction coefficients between the sheets were measured. The measurement was made under conditions of a temperature of 25° C., a moving velocity of the contact pad of 5 mm/second and a load of 25 g/cm$^2$. The results were evaluated based on the following standard.

⊚: 10.0 or more
○: 5.0 to 10.0
X: less than 5.0

TABLE 1

| | Z | Alkylene oxide molar number added (mol) EO | PO | Weight ratio of EO in AO (weight %) | n | x | x × n | Molecular weight |
|---|---|---|---|---|---|---|---|---|
| lamination aid 1 | n-butyl alcohol | 0 | 50 | 0 | 50 | 1 | 50 | 3,000 |
| lamination aid 2 | n-butyl alcohol | 0 | 85 | 0 | 85 | 1 | 85 | 5,000 |
| lamination aid 3 | n-butyl alcohol | 45 | 50 | 40 | 95 | 1 | 95 | 5,000 |
| lamination aid 4 | ethylene glycol | 315 | 80 | 75 | 198 | 2 | 395 | 18,500 |
| lamination aid 5 | glycerin | 0 | 84 | 0 | 28 | 3 | 84 | 5,000 |
| lamination aid 6 | 3,5,5,-trimethyl hexanol | 8 | 3 | 65 | 11 | 1 | 11 | 670 |
| lamination aid 7 | 3,5,5,-trimethyl hexanol | 3 | 10 | 20 | 13 | 1 | 13 | 860 |
| Comparative article 1 | ethylene glycol | 10 | 0 | 100 | 5 | 2 | 10 | 400 |
| Comparative article 2 | ethylene glycol | 450 | 0 | 100 | 225 | 2 | 450 | 20,000 |

TABLE 2

| Test example | | Inventive Example 1 | Inventive Example 2 | Inventive Example 3 | Inventive Example 4 | Inventive Example 5 | Inventive Example 6 |
|---|---|---|---|---|---|---|---|
| Component (A) | lamination aid 1 | 0.4 | | | | | 0.4 |
| | lamination aid 2 | | 0.4 | | | | |
| | lamination aid 3 | | | 0.4 | | | |
| | lamination aid 4 | | | | 0.2 | | |
| | lamination aid 5 | | | | | 0.6 | |
| | lamination aid 6 | | | | | | |
| | lamination aid 7 | | | | | | |
| Component (A)' | Comparative article 1 | | | | | | |
| | Comparative article 2 | | | | | | |
| Component (B) | Polyvinyl butyral supplied by Sekisui Chemical Co. Ltd. "BH-3" (Weight average molecular weight = 110,000) | 6.9 | 6.9 | 6.9 | 6.9 | 6.9 | 6.9 |
| Component (C) | barium titanate powder (Average particle size 200 μm) | 92.7 | 92.7 | 92.7 | 92.9 | 92.5 | 92.7 |
| total amount | Total of (A) + (B) + (C); mass % | 100 | 100 | 100 | 100 | 100 | 100 |
| | The other components | Unit: mass parts with respect to 100 mass parts of (A) + (B) + (C) | | | | | |
| Plasticzer | dibutyl phthalate | 0 | 0 | 0 | 0 | 0 | 1.5 |
| Dispersant | Maliulim SC-0505K | 1.0 | | | | | |
| Solvent | Toluene/Ethanol = 50 wt/50 wt | 120 | | | | | |
| Evaluation | Sheet strength [N/mm²] | 16.8 ◎ | 17.0 ◎ | 16.7 ◎ | 16.4 ◎ | 16.9 ◎ | 16.8 ◎ |
| | Adhesive strength [N/m] | 13.1 ○ | 13.7 ○ | 14.1 ○ | 14.5 ○ | 13.8 ○ | 17.0 ◎ |
| | Static friction coefficient | 7.9 ○ | 10.2 ◎ | 8.2 ○ | 9.6 ○ | 10.3 ◎ | 8.1 ○ |

TABLE 3

| Test examples | | Inventive Example 7 | Inventive Example 8 | Inventive Example 9 | Inventive Example 10 | Inventive Example 11 |
|---|---|---|---|---|---|---|
| Component (A) | lamination aid 1 | | | | | |
| | lamination aid 2 | 0.4 | | | | |
| | lamination aid 3 | | 0.4 | | | |
| | lamination aid 4 | | | | | |
| | lamination aid 5 | | | | | |
| | lamination aid 6 | | | 1.5 | | |
| | lamination aid 7 | | | | 1.5 | 0.7 |
| Component (A)' | Comparative article 1 | | | | | |
| | Comparative article 2 | | | | | |
| Component (B) | Polyvinyl butyral supplied by Sekisui Chemical Co. Ltd. "BH-3" (Weight average molecular weight = 110,000) | 6.9 | 6.9 | 6.9 | 6.9 | 6.9 |
| Component (C) | barium titanate powder (Average particle size 200 μm) | 92.7 | 92.7 | 91.6 | 91.6 | 92.4 |
| Total amount | Total of (A) + (B) + (C); mass % | 100 | 100 | 100 | 100 | 100 |
| | The other components | Unit: mass parts with respect to 100 mass parts of (A) + (B) + (C) | | | | |

TABLE 3-continued

| Test examples | | Inventive Example 7 | Inventive Example 8 | Inventive Example 9 | Inventive Example 10 | Inventive Example 11 |
|---|---|---|---|---|---|---|
| Plasticzer | dibutyl phthalate | 1.5 | 1.5 | 0 | 0 | 0.7 |
| Dispersant | Maliulim SC-0505K | | | 1.0 | | |
| Solvent | Toluene/Ethanol = 50 wt/50 wt | | | 120 | | |
| Evaluation | Sheet strength [N/mm²] | 16.9 ◎ | 16.5 ◎ | 16.1 ◎ | 16.3 ◎ | 16.4 ◎ |
| | Adhesive strength [N/m] | 17.7 ◎ | 18.2 ◎ | 14.3 ○ | 13.5 ○ | 13.8 ○ |
| | Static friction coefficient | 10.7 ◎ | 8.9 ○ | 8.5 ○ | 9.5 ○ | 9.7 ○ |

TABLE 4

| Test examples | | Comparative Example 1 | Comparative Example 2 | Comparative Example 3 | Comparative Example 4 |
|---|---|---|---|---|---|
| 成分 (A) | lamination aid 1 | | | | |
| | lamination aid 2 | | | | |
| | lamination aid 3 | | | | |
| | lamination aid 4 | | | | |
| | lamination aid 5 | | | | |
| | lamination aid 6 | | | | |
| | lamination aid 7 | | | | |
| Component (A)' | Comparative article 1 | 0.4 | | | |
| | Comparative article 2 | | 0.4 | | |
| Component (B) | Polyvinyl butyral supplied by Sekisui Chemical Co. Ltd. "BH-3" (Weight average molecular weight = 110,000) | 6.9 | 6.9 | 7.0 | 6.9 |
| Component (C) | barium titanate powder (Average particle size 200 μm) | 92.7 | 92.7 | 93.0 | 93.1 |
| Total amount | Total of (A) + (B) + (C); mass % | 100 | 100 | 100 | 100 |
| | The other components | Unit: mass parts with respect to 100 mass parts of (A) + (B) + (C) | | | |
| Plasticzer | dibutyl phthalate | 0 | 0 | 0 | 1.5 |
| Dispersant | Maliulim SC-0505K | | | 1.0 | |
| Solvent | Toluene/Ethanol = 50 wt/50 wt | | | 120 | |
| Evaluation | Sheet strength [N/mm²] | 14.1 X | 16.3 ◎ | 16.6 ◎ | 16.3 ◎ |
| | Adhesive strength [N/m] | 7.5 X | 5.1 X | 5.2 X | 7.2 X |
| | Static friction coefficient | 0.9 X | 0.8 X | 0.8 X | 0.9 X |

(Molding 2 of Ceramic Green Sheet)

The sheet properties and adhesive properties were evaluated as the molding 1 except that barium titanate powder used in the molding 1 of the ceramic green sheet was changed to alumina powder. The results were shown in table 5.

TABLE 5

| Test examples | | Inventive Example 12 | Inventive Example 13 | Comparative Example 5 |
|---|---|---|---|---|
| Component (A) | lamination aid 1 | | | |
| | lamination aid 2 | 0.4 | | |
| | lamination aid 3 | | | |
| | lamination aid 4 | | | |
| | lamination aid 5 | | | |
| | lamination aid 6 | | 0.7 | |
| | lamination aid 7 | | | |
| Component (A)' | Comparative article 1 | | | 0.4 |
| | Comparative article 2 | | | |
| Component (B) | Polyvinyl butyral supplied by Sekisui Chemical Co. Ltd. "BH-3" (Weight average molecular weight = 110,000) | 6.9 | 6.9 | 6.9 |

TABLE 5-continued

| Test examples | | Inventive Example 12 | Inventive Example 13 | Comparative Example 5 |
|---|---|---|---|---|
| Component (C) | Alumina powder (Average grain size 170 μm) | 92.7 | 92.4 | 92.7 |
| Total amount | Total of (A) + (B) + (C); mass % | 100 | 100 | 100 |
| | The other components | Unit: mass parts with respect to 100 mass parts of (A) + (B) + (C) | | |
| Plasticzer | dibutyl phthalate | 0 | 0.7 | 0 |
| Dispersant | Maliulim SC-0505K | | 1.0 | |
| Solvent | Toluene/Ethanol = 50 wt/50 wt | | 120 | |
| Evaluation | Sheet strength [N/mm²] | 16.8 ◎ | 16.1 ◎ | 13.5 X |
| | Adhesive strength [N/m] | 13.5 ○ | 14.5 ○ | 7.5 X |
| | Static friction coefficient | 10.3 ◎ | 9.9 ○ | 1.3 X |

As can be seen from the results shown in tables 2, 3, 4 and 5, according to the inventive examples 1 to 13, good results were obtained in the sheet strength, adhesive strength and static friction coefficient.

On the other hand, according to the comparative examples 1 and 5, as the weight ratio of EO contained in AO is out of the range of the present invention, sufficient static friction coefficient were not be obtained and sheet strength is lowered.

According to the comparative example 2, the weight ratio of EO contained in AO is out of the range of the present invention, sufficient adhesive strength and static friction coefficient were not obtained.

According to the comparative examples 3 and 4, as the lamination aid was not contained, the adhesion strength and static friction coefficient were insufficient.

The invention claimed is:

1. A ceramic green sheet composition comprising 0.01 to 5 mass % of a component (A) described below, 1 to 25 mass % of a component (B) described below, 70 to 98 mass % of a component (C) described below, and a polymer dispersant comprising a polyether group and a carboxyl group, said polymer dispersant being contained in a ratio of 0.1 to 10 mass parts with respect to 100 mass parts of a total amount of said component (A), said component (B) and said component (C), said component (A): a lamination aid for a ceramic green sheet, said lamination aid comprising a compound represented by a formula (1), and said lamination aid suppressing lamination misalignment of said ceramic green sheet:

$$Z—[O-(AO)n-H]x \qquad (1)$$

wherein in the formula (1),

Z represents a residual group of 3, 5, 5-trimethyl hexanol having a hydroxyl group of 1 in which said hydroxyl group is removed;

x represents a number of 1;

AO represents an oxyalkylene group having a number of carbons of 2 to 3, said oxyalkylene group AO comprising oxyethylene group EO and oxypropylene group PO;

n represents a number of 5 to 500;

x×n is in a range of 5 to 500;

wherein said oxyethylene group EO and said oxypropylene group PO are added in block addition mode, and a weight ratio of oxyethylene group EO contained in said oxyalkylene group AO having the number of carbons of 2 to 3 is 80 weight % or lower, said component (B): polyvinyl butyral; and said component (C): ceramic powder.

2. The ceramic green sheet composition of claim 1, wherein the average molar number added (x×n) of all the AO's in the formula (1) is 10 to 450.

3. The ceramic green sheet composition of claim 1, wherein the weight ratio of said oxyethylene group EO contained in said oxyalkylene group AO is 65 weight % or lower.

* * * * *